United States Patent [19]
Stuart et al.

[11] Patent Number: 5,610,068
[45] Date of Patent: Mar. 11, 1997

[54] FIELD METHOD FOR DETERMINING IF ADEQUATE CORROSION INHIBITION HAS BEEN APPLIED TO THERMALLY PROCESSED CANS

[75] Inventors: Christine M. Stuart, Wheaton; Deborah M. Rogers, Naperville; James R. Van Camp, Glen Ellyn, all of Ill.; Michael P. Sowinski, Gig Harbor, Wash.

[73] Assignee: Nalco Chemical Company, Naperville, Ill.

[21] Appl. No.: 508,655

[22] Filed: Jul. 28, 1995

[51] Int. Cl.$^6$ .................................................. G01N 17/00
[52] U.S. Cl. ................................................ 436/6; 422/53
[58] Field of Search ........................ 73/86; 422/53; 436/6

[56] References Cited

U.S. PATENT DOCUMENTS

| | | |
|---|---|---|
| 2,351,644 | 6/1944 | Talley et al. . |
| 2,987,685 | 6/1961 | Schaschl ................... 73/86 X |
| 3,019,090 | 1/1962 | Renshaw et al. . |
| 3,236,599 | 2/1966 | Fowler et al. . |
| 3,397,964 | 8/1968 | Zall . |
| 3,711,249 | 1/1975 | Keeney ................... 422/53 X |
| 4,067,751 | 1/1978 | Pistulka ................... 73/104 X |
| 4,671,933 | 6/1987 | Lengnick et al. ............ 422/9 |
| 5,275,760 | 1/1994 | Johnson ................ 252/389.61 |

FOREIGN PATENT DOCUMENTS

| | | | |
|---|---|---|---|
| 610003 | 8/1994 | European Pat. Off. ........ 422/53 |
| 160268 | 6/1994 | Japan ....................... 422/53 |
| 235692 | 8/1994 | Japan ....................... 422/53 |
| 1663513 | 7/1991 | U.S.S.R. ...................... 436/6 |

OTHER PUBLICATIONS

*Patent Abstracts of Japan* "Anticorrosive Coating for Frequently Seawater Splashed Area of Marine Steel Structure": Grp M040, vol. 4, No. 161 Abs Pub. date Nov. 11, 1980 (55–111232).

*Primary Examiner*—Thomas P. Noland
*Attorney, Agent, or Firm*—Robert A. Miller; Patricia A. Charlier; James J. Drake

[57] ABSTRACT

A method for determining the adequacy of corrosion prevention treatments applied to metal surfaces is disclosed. The method provides a qualitative determination of corrosion detection using inexpensive equipment. Generally, the method encompasses wetting at least a first and a second absorbent patches capable of retaining a liquid corrosive to metal surfaces to be tested with the corrosive liquid to obtain wetted patches and then contacting a portion of a first metal surface to be tested with the first patch under corrosive conditions and contacting a portion of a second metal surface to be tested with the second patch, wherein the second metal surface having the same composition as the first metal surface has been treated with an effective amount of a corrosion prevention treatment and subjecting the second patch in contact with the second metal surface to the same corrosive conditions as the corrosive conditions applied to the first patch in contact with the first metal surface. The method includes removing the first and the second patches from the first and the second metal surfaces; respectively and, treating the first and the second patches with an effective amount of a tetrazolium compound; and, comparing the amount of stain present on the first patch with the amount of stain present on the second patch, wherein the efficacy of the corrosion prevention treatment can be qualitatively determined.

4 Claims, 1 Drawing Sheet

Test

Corrosion Free Days

Dosage (ppm 3008)

110 degrees F - 50% Relative Humidity

FIELD METHOD FOR DETERMINING IF ADEQUATE CORROSION INHIBITION HAS BEEN APPLIED TO THERMALLY PROCESSED CANS

BACKGROUND OF THE INVENTION

1. Field of the Invention

The invention relates to a novel method of determining corrosion efficacy of various treatment compounds and, more particularly, to a patch test for determining the efficacy of corrosion inhibitors used for metal cans.

2. Description of the Prior Art

Determination of the efficacy of corrosion prevention treatments applied to metal surfaces is of great importance to industry. The use of metal surfaces which have been improperly treated with corrosion prevention coatings lead to short shelf lives of goods fabricated using these metals. Cans containing foodstuffs which are improperly treated for corrosion prevention during the cooking or cooling process corrode, and while this condition does not bring into direct question the quality of the foodstuff contained in the can, goods look unappealing and unappetizing resulting in their removal from store shelves and their eventual destruction.

Current corrosion testing means are time consuming and do not offer a rapid indication of whether or not metal surfaces, including cans, have been properly treated so that they may attain the longest possible shelf life without visible deterioration due to corrosion. Examples of current tests employed to determine the effect of corrosion prevention treatments include the use of corrosion coupons which are exposed to air (or water) for lengthy periods of time and then carefully weighed to determine metal loss, the use of an apparatus such as a Cleveland humidity cabinet which provides high humidity environments for the exposure of treated metal surfaces over long periods of time, and the exposure of samples of the treated goods to the atmosphere.

All of these treatment methods are time consuming and, as a result of the time taken, by the time a defect, or improperly treated specimen is determined, the goods so treated have frequently been shipped to a customer or further processed.

SUMMARY OF THE INVENTION

The present invention provides a test method for determining the adequacy of corrosion prevention treatments applied to metal surfaces is disclosed. The method provides a quantitative determination of corrosion detection using inexpensive equipment. Generally, the method encompasses:

a) wetting at least a first and a second absorbent patches capable of retaining a liquid corrosive to metal surfaces to be tested with the corrosive liquid to obtain wetted patches;

b) contacting a portion of a first metal surface to be tested with the first patch under corrosive conditions;

c) contacting a portion of the second, metal surface to be tested with the second patch, wherein the second metal surface having the same composition as the first metal surface has been treated with an effective amount of a corrosion prevention treatment;

d) subjecting the second patch in contact with the second metal surface to the same corrosive conditions as the corrosive conditions applied to the first patch in contact with the first metal surface;

e) removing the first and second patches from the first and the second metal surfaces, respectively;

f) comparing the amount of stain present on the first patch with the amount of stain present on the second patch, whereby the efficacy of the corrosion prevention treatment can be qualitatively determined; and/or, f') reacting the corrosion products on the first and the second patches in a Ferrosine® solution. Ferrosine® will remove the iron from the patch by reacting with the iron to form an new compound that absorbs light at ~560 nm. The resultant purple colored solution is analyzed photometrically to quantitatively determine the iron content of the patch.

Alternatively, the metal surface exposed when the patch is removed can be examined and compared with the metal surface similarly tested which had been properly treated with a corrosion preventive material.

DESCRIPTION OF THE INVENTION

Figure 1:
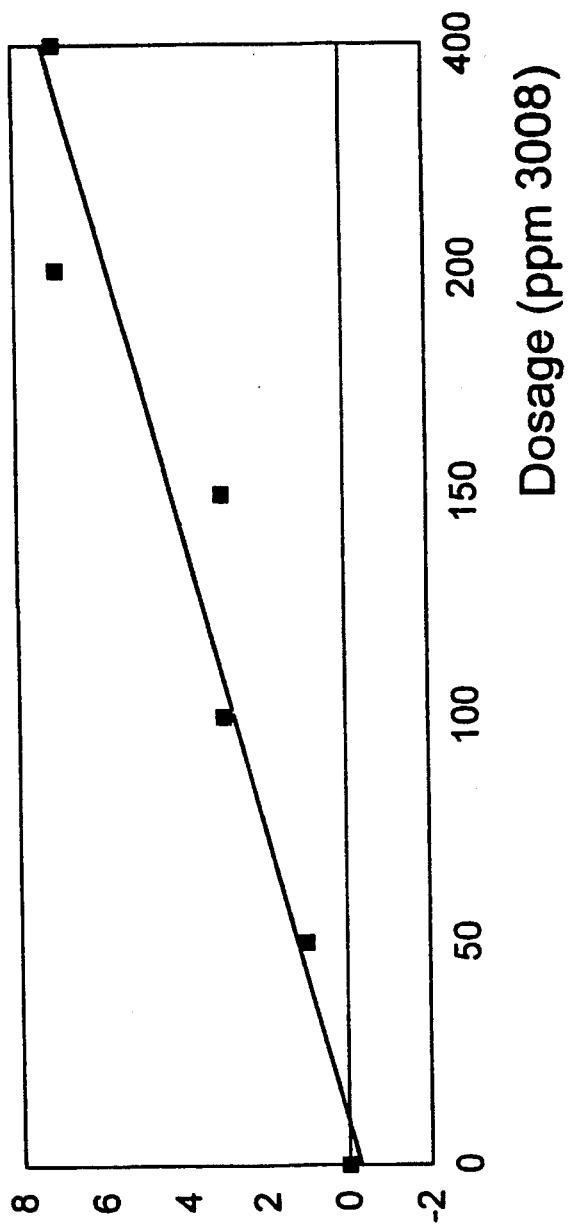
FIG. 1 is a graph illustrating corrosion free days based on dosage.

The present invention provides a test method for determining the efficacy of a corrosion prevention treatment on a metal surface on a qualitative and/or quantitative basis. The test method employed is inexpensive, produces results in time periods ranging from as little as seconds to about four hours, can be easily carried out without the use of expensive laboratory equipment, and provides a reproducible means to determine the efficacy of corrosion prevention treatments.

The basic method of this invention is set forth in the following six steps:

(a) wetting at least a first and a second absorbent patches capable of retaining a liquid corrosive to metal surfaces to be tested with the corrosive liquid to obtain wetted patches;

(b) contacting a portion of a first metal surface to be tested with the first patch under corrosive conditions;

(c) contacting a portion of a second metal surface to be tested with the second patch, wherein the second metal surface having the same composition as the first metal surface has been treated with an effective amount of a corrosion prevention treatment;

(d) subjecting the second patch in contact with the second metal surface to the same corrosive conditions as the corrosive conditions applied to the first patch in contact with the first metal surface;

(e) removing the first and the second patches from the first and the second metal surfaces, respectively; and, (f) comparing the amount of stain present on the first patch with the amount of stain present on the second patch, wherein the efficacy of the corrosion prevention treatment can be qualitatively determined.

Step (f) above can be replaced by the following alternate step (f'):

(f') comparing the amount of stain present on the portion of the first metal surface which had been in contact with the first patch to the amount of stain present on the second metal surface which had been in contact with the second patch, whereby the efficacy of the corrosion prevention treatment can be qualitatively determined. This alternate step (f') can also be performed in addition to step (f) above.

In addition, steps (f) and (f') can be replaced by the following steps (g) and (h):

(g) treating the first and second patches with an effective amount of a tetrazolium compound; and (h) comparing the amount of stain present on the first patch to the amount of stain on the second patch, whereby the efficacy of the corrosion prevention treatment can be qualitatively determined.

Alternatively, steps (a), (g) and (h) can be replaced by the following steps (a') and (g'):

(a') wetting at least a first and second patches capable of retaining a liquid corrosive to metal surfaces to be tested with the corrosive liquid containing an effective amount of a tetrazolium compound to obtain wetted patches;

(g') comparing the amount of stain present on the first patch to the amount of stain on the second patch, whereby the efficacy of the corrosion prevention treatment can be qualitatively determined.

In addition, a quantitative analysis can be carried out by the following seven steps:

1) wetting at least a first and a second absorbent patches capable of retaining a liquid corrosive to metal surfaces to be tested with the corrosive liquid to obtain wetted patches;

2) contacting a portion of a first metal surface to be tested with the first patch under corrosive conditions;

3) contacting a portion of a second metal surface to be tested with the second patch, wherein the second metal surface having the same composition as the first metal surface has been treated with an effective amount of a corrosion prevention treatment;

4) subjecting the second patch in contact with the second metal surface to the same corrosive conditions as the corrosive conditions applied to the first patch in contact with the first metal surface;

5) removing the first and the second patches from the first and the second metal surfaces, respectively;

6) treating the first and the second patches, separately, with an effective amount of Ferrosine® solution to produce a first and a second purple colored solutions, respectively; and, 7) photometrically analyzing the first and the second purple colored solutions at about 560 nm, wherein iron content of the first and the second solutions can be quantitatively determined.

The corrosion detection patch comprises a patch of cellulosic or any other absorbent material capable of absorbing a corrosive liquid. This patch is adapted to be placed on a metal surface, maintained in position for a period of time, and then removed so that the metal surface which has been in contact with the patch or the patch itself can be examined for staining or the like.

Alternatively, a tetrazolium compound can be added to the liquid corrosive used to wet the patch. Tetrazolium compounds change colors when reduced, whereby the resulting blue to purple color is indicative of corrosion occurring on the can. The blue to purple color will develop in areas where the patch contains iron. By-products from the corrosion process of iron typically are a light orange color in the presence of low levels of iron which makes the qualitative comparison between patches difficult. These blue to purple colors resulting from the addition of a tetrazolium compound are more easily discernible than the light orange color that would typically be observed on such patches. Typical solutions used in the tests contained about 20 p.p.m. of a tetrazolium compound. Tetrazolium compounds, such as Tetranitro Blue Tetrozolium, Tetrazolium Violet, Tetrazolium Blue Chloride, Nitro Blue Tetrazoluim Chloride, and Triphenyl-Tetrazolium solutions, are available from the Hach Chemical Company.

The metal surfaces to which this invention is applicable include metal surfaces of all commonly available metals typically encountered in the fabrication of metallic articles. Such metals include, but are not limited to, steel, tin coated steel, aluminum, and other metals. While this invention is particularly adapted to determine the efficacy of a corrosion prevention treatment applied to tin coated steel cans containing foodstuffs during the can cooking or cooling processes, this invention should also perform satisfactorily on other metallic surfaces to which a corrosion prevention treatment has been applied. Of particular note, and in a preferred embodiment of this invention, the metal surface which is tested may involve a weld or seam, such as the weld or can chime typically found on tin coated steel or steel cans.

The absorbent patch used in this invention to determine the effect of a corrosion prevention treatment may be fabricated from a number of different types of materials. These materials include synthetic polymeric superabsorbents, gauze pads of adhesive bandage strips, and cellulosic fiber mats including filter paper, absorbent tissue or toweling, cotton, and wool as well as any other absorbent materials which are pliable, capable of retaining a corrosive liquid, and stable while retaining the corrosive liquid for the period of time that the patches remain in contact with the metal surfaces. In practicing the embodiment of the test method where it is desirable to examine the patch for corrosion byproducts, light, uniformly colored, preferably white patches are preferred. In a preferred embodiment of this invention, absorbent toweling, tissue or filter paper is employed. Most preferably, a gauze pad such as that found in an ordinary adhesive bandage strip is used. An example of such an adhesive bandage strip containing a gauze or gauze-like material which worked well in the practice of this invention is the Curity Curad all-purpose plastic strip which the manufacturer states has a "Telfa-Pad®", a highly absorbent cushion pad which is covered by a soft perforated film. The Curity Curad adhesive bandage strips are available from the Kendall-Futuro Division of the Kendall Company, Cincinnati, Ohio. Band-Aid Brand Adhesive Strips available from the Johnson and Johnson Corporation are also useful in the practice of this invention.

The absorbent patch material described above must be maintained in contact with the metal surface for the duration of the test period. In fastening the absorbent patch material to the metal surface, it is important that the side of the patch material not contacting the metal surface be open to the atmosphere, and must be allowed to "breathe". Thus, the absorbent patch material may not be totally covered with an impervious tape, and should be covered only with a substance which allows the atmosphere of the container into which the metal article is placed to have direct contact with the absorbent patch material. In a most preferred embodiment of this invention, the absorbent patch material a one-piece adhesive bandage strip where the absorbent material is held in place with an adhesive strip having a porous center which is placed directly over the patch. Commonly available adhesive bandage strips such as those used for dressing small cuts or abrasions and sold under the tradenames stated above are preferred. This type of strip avoids the problem of separately fastening an absorbent patch and adhesive.

In another embodiment of this invention, an adhesive strip such as those described above is used to fasten an absorbent paper, preferably an ashless filter paper, to the metal surface. Thus a piece of filter paper may be cut slightly larger than the pad area of the adhesive strip and placed on the strip.

After fastening the absorbent patch to the metal surface to be tested so that the absorbent patch communicates to the metal surface, the absorbent is wet with a liquid corrosive to the metal surface. The corrosive liquid employed may vary considerably depending upon the end use to which the metal article is to be put, the metal used, the method of analysis (quantitative vs qualitative method) as well as the particular corrosion prevention treatment applied. Typical liquids which are corrosive to the metal surface useful in this invention contain from about 50 to about 2,000 p.p.m. of chloride anion and have a pH value ranging from about 2 to about 8. It should be noted that while it is preferable to use a solution containing chloride anions for the efficacy determination of a corrosion prevention treatments applied to tin cans during the cooking process, aqueous solutions containing other corrosion causing anions including sulphate, nitrate, sulfite, bromide, phosphate, and the like, may be prepared and utilized. Mixtures of such anions may also be employed. Cations present in the solution are generally alkali or alkaline earth metal ions. While the preferred pH value of this invention ranges from about 2 to about 8, the pH value actually used should be based on the type of metallurgy being evaluated and the use to which the metal surface being evaluated will be employed. As an example, if a metal surface will be exposed to alkali, it may be beneficial to test at higher pH values and vary the corrosive liquid to contain alkali or alkaline earth metal hydroxides. It should be noted that while it is preferable to use a Ferrosine® solution for the quantitative efficacy determination of corrosion prevention treatments applied to tin cans during the cooking or cooling process, other methods of determining iron or corrosion by-products could also be used to quantity corrosion rates. The Ferrosine solution is available from the Hach Chemical Company.

Due to the nature of the test employed, it is preferred that a solution highly corrosive to the metal surface being tested is used so that testing is accelerated. Because it is important in the testing process be reproducible, the composition of the solution, the test duration, as well as the volume of the liquid corrosive used per test should be noted so that the test results can be fairly compared.

The metal surfaces, both treated and untreated with a corrosion prevention material, having patches containing liquid corrosive fastened to the such surfaces, are exposed to a high humidity atmosphere and a corrosive temperature for a time sufficient to allow corrosion of improperly treated surfaces to occur. The corrosive temperature may range from about 20° to about 100° C. at humidities of from about 20% to about 98%. More preferably, the corrosive temperature may range from about 25° to about 80° C. A most preferred corrosive temperature ranges from about 40° to about 80° C. In order to maintain a constant high humidity condition, the metal surface may be sealed an impervious container such as a plastic bag. While a container consisting of a plastic bag provides a preferred method of carrying out the test method of this invention, other more elaborate equipment, such as incubators, constant temperature drying ovens, and the like, may be employed in the practice of this invention. When using a plastic bag, it is preferred to seal the bag using a rubber band, rope, wire, or the like.

After a period of time, typically from about 10 minutes to about 4 hours and more preferably from about 10 minutes to about 30 minutes for the qualitative method and from about 2 hours to about 4 hours for the quantitative method, the metal surface, having the absorbent patch fastened thereto, is removed from the corrosive atmosphere and the patch is then removed from the metal surface. Examination of the metal surface exposed when the patch is removed, or the surface of the patch that had been in contact with the metal surface, for the presence of stain or corrosion by-products which provides an immediate, rapid, qualitative determination of the presence of corrosion. By comparing the amount of stain present on the exposed metal surface or the patch to the stain present on an exposed surface of a treated metal surface which has been similarly tested (or a patch removed from a metal surface similarly treated), the efficacy of the corrosion prevention treatment applied to the treated metal surface can be determined.

Alternatively, the iron concentration on the patch can be quantitatively determined by reacting the patch with a Ferrosine® solution to produce a purple solution which can be analyzed photometrically. The iron concentrations in the patch can be quantitatively determined using this method. The corrosion by-products found in the patch are quantitatively determined and can be compared to tests of other similarly processed cans to evaluate the effectiveness of a corrosion inhibitor. The best corrosion inhibitor packages reduce or prevent corrosion of the metal which result in lower iron concentrations in the patches. In order to determine the efficacy of the qualitative and quantitative test methods of this invention, the following tests were conducted.

The following examples are presented to describe preferred embodiments and utilities of the invention and are not meant to limit the invention unless otherwise stated in the claims appended hereto.

EXAMPLE 1

An aqueous corrosion causing solution containing 1500 p.p.m. sodium chloride in distilled water was prepared. Curad plastic adhesive bandage strips were obtained and the pad or "Telfa-Pad"® portion of a bandage strip was wet with a small known volume of the sodium chloride solution. The adhesive bandage strip was then placed on treated tin coated steel cans with the patch or pad portion being placed over the seam of each can. The cans were each sealed in a plastic bag, and placed in a 100° F. oven for a period of sixty minutes. After sixty minutes, each bag was removed from the incubator, opened, the can removed, and the bandage strip removed from the can. If the metal surface underneath the patch was clean, corrosion prevention was deemed to be sufficient. If the metal is orange to rust colored, corrosion has taken place and corrosion prevention was deemed insufficient. Likewise, of the portion if the patch having been in contact with the metal surface shows no discoloration from metal corrosion by-products, corrosion prevention is deemed adequate. If the portion of the patch which was in contact with the metal surface shows discoloration from metal corrosion by-products (colored metallic oxides and chlorides), corrosion prevention is judged insufficient. The patch was applied over the can seam, since this is the weakest portion of the can and during the welding process, the tin is often stripped off leaving mild steel exposed.

The following test data shows the use of the above procedure on cans taken directly from a commercial cannery. Some of the cans that were evaluated were treated with a proprietary multi-functional corrosion inhibitor solution available from Nalco Chemical Company, Naperville, Ill.

and sold under the trade mane NALCO® 3008 (N-3008). By placing the can in a 1,500 p.p.m. solution of the corrosion inhibitor at 180° for one hour prior to testing the following results of the tests are shown below:

TABLE I

| Exposure Time | Temp. of Incubator | Patch Water | Can Treatment | Result (1)* |
| --- | --- | --- | --- | --- |
| 1.5 hr. | 37° C. | 1500 Cl-pH 2.7 | None | Spot |
| 1.5 hr. | Rm. Temp. | 1500 Cl-pH 2.7 | None | Spot |
| 1.5 hr. | Rm. Temp. | 1500 Cl-pH 2.7 | 1500 ppm N-3008 | Spot |
| 1.0 hr. | Rm. Temp. | 1500 Cl-pH 2.7 | None | Spot |
| 35 min. | Rm. Temp. | 1500 Cl-pH 6.0 | None | Clean |
| 35 min. | Rm. Temp. | 1500 Cl-pH 6.0 | 1500 ppm N-3008 | Clean |
| 1 hr. | Rm. Temp. | 1500 Cl-pH 6.0 | 1500 ppm N-3008 | Clean |
| 1 hr. | Rm. Temp. | 1500 Cl-pH 6.0 | None | Spot |
| 30 min. | 37° C. | 1500 Cl-pH 6.0 | 1500 ppm N-3008 | Clean |
| 30 min. | 37° C. | 1500 Cl-pH 6.0 | None | Spot |
| 1 hr. | 37° C. | 1500 Cl-pH 6.0 | None | Spot |
| 1 hr. | 37° C. | 1500 Cl-pH 6.0 | 1500 ppm N-3008 | Clean |
| 1 hr. | 37° C. | 1500 Cl-pH 6.0 | 400 ppm N-3008 | Spot |
| 1 hr. | 37° C. | 1500 Cl-pH 6.0 | None | Clean |
| 1 hr. | 37° C. | 1500 Cl-pH 6.0 | 450 ppm N-3008 | Clean |
| 1 hr. | 37° C. | 1500 Cl-pH 6.0 | 450 ppm N-3008 | Clean |

*(1) VISUAL OBSERVATION OF THE PATCH

EXAMPLE 2

The corrosion patch test, as described above, was used to measure the effect of reducing the concentration of a neutralizing amine being fed to a commercially available rust preventative which did not contain an amine. The rust preventative was fed at a constant pump rate. The pH was monitored and the "patch test" was used to evaluate can prevention. At the start of the test, the can cooker water had a pH value of 6.6 and cans produced at that time showed no evidence of corrosion using the patch test. Fifteen minutes later, the pH of the can cooker had been lowered to a value of 5.3 and the patch test showed slight spotting. At 1 hr. and 45 min. after the start of the test, the pH of the can cooker had fallen to a value of 4.7 and cans tested showed evident side seam stains. The test was terminated at 1 hr. and 45 min. because of the likelihood of further corrosion. These tests provided a good correlation between results of the patch test and the expected corrosion prevention of treated cans.

EXAMPLE 3

In yet another testing situation, cans from a commercial cannery were treated to provide extra corrosion prevention using a corrosion inhibitor that was sprayed onto the cans immediately after being processed in the can cooker and while the cans were still warm from the cooking process. It was estimated that the cans were the temperature of 100° F. at the time of treatment. Duplicate patch tests, run in the manner described above, show that the cans were properly treated. The absorbent patches exhibited no signs of staining. However, when the corrosive liquid applied to the patches was changed to a dilute solution of sulfuric acid, the patch tests showed that seams of the can were severely affected as indicated by a substantial stain. This indicates that the corrosion prevention was not adequate in the event that the finished product would have been exposed to severe corrosive conditions of this type.

As applied to cans, it should be noted that if a can exhibits a spot and it was expected to pass as a result of being treated, the can could have been accidentally damaged during processing. Therefore, the test should be run in duplicate in an effort to eliminate false positive results.

EXAMPLE 4

Unsealed three piece tin plated mild steel cans were filled with hot deionized water. Each can was then sealed by crimping a can lid in place with a can sealer. The cans were each placed in a beaker containing: 144 p.p.m. calcium, 48 p.p.m. magnesium, 264 p.p.m. alkalinity (all as calcium carbonate), and a corrosion inhibitor. The N-3008 corrosion inhibitor package (a molybdate/nitrite based program) was dosed at 0, 50, 100, 150, 200, and 400 p.p.m. The beakers were then placed in a water bath and processed at 205° F. for 45 minutes. After processing, cans were removed from the water bath and a quantitative patch test was conducted on each can using the procedure described above. Four duplicate runs were conducted and results averaged.

| N-3008 Dosage - ppm | Average Iron Concentration - [ppb] | % Iron Reduction |
| --- | --- | --- |
| 0 | 337 | 0 |
| 50 | 344 | 0 |
| 100 | 283 | 16 |
| 150 | 268 | 21 |
| 200 | 224 | 34 |
| 400 | 111 | 67 |

Corrosion rates using the patch test were compared to results from experiments conducted in a humidity chamber. The cans were again processed in a water bath using the process described above. After processing, the cans were immediately placed in a humidity chamber set at about 110° F. and about 50% humidity. The cans were monitored to determine the number of days the cans showed no visible signs of corrosion. FIG. 1 shows corrosion-free days and quantitative patch test iron levels versus N-3008 dosage. The patch test results correlate well with results from the humidity chamber experiment.

Based upon the above results, it was determined that the patch test of this invention gave a rapid, reproducible, qualitative determination of the efficacy of the corrosion prevention treatment applied to cans of foodstuff at commercial canneries. While the examples directed to this invention deal specifically with cans treated in a can cooker, the test should find equal applicability on other metal surfaces.

Changes can be made in the composition, operation and arrangement of the method of the present invention described herein without departing from the concept and scope of the invention as defined in the following claims:

We claim:

1. A method of determining the efficacy of a corrosion prevention treatment applied to a metal surface which comprises:

a) wetting at least a first and a second absorbent patches capable of retaining a liquid corrosive to metal surfaces to be tested with the corrosive liquid to obtain wetted patches;

b) contacting a portion of a first metal surface to be tested with the first patch under corrosive conditions;

c) contacting a portion of a second metal surface to be tested with the second patch, wherein the second metal surface having the same composition as the first metal surface has been treated with an effective amount of a corrosion prevention treatment;

d) subjecting the second patch in contact with the second metal surface to the same corrosive conditions as the corrosive conditions applied to the first patch in contact with the first metal surface;

e) removing the first and the second patches from the first and the second metal surfaces, respectively;

f) treating the first and the second patches with an effective amount of a tetrazolium compound; and, g) comparing the amount of stain present on the first patch to the amount of stain present on the second patch, whereby the efficacy of the corrosion prevention treatment can be qualitatively determined.

2. The method according to claim 1, wherein the corrosive liquid to the metal surfaces is an aqueous fluid containing from about 50 to about 2,000 p.p.m. chloride anion and having a pH value of from about 2 to about 8.

3. The method according to claim 1, wherein the corrosive conditions are maintained for a time period of from about 10 minutes to about 2 hours at a temperature of from about 20° to about 100° C.

4. The method according to claim 1, wherein the absorbent patch is selected from the group consisting of: adhesive bandage strips; synthetic polymeric superabsorbents; and, cellulosic fiber mats.

* * * * *